(12) United States Patent
Senegas et al.

(10) Patent No.: US 12,165,761 B2
(45) Date of Patent: Dec. 10, 2024

(54) SELF-LEARNING DISTRIBUTED SYSTEM WITH AUTOMATED GROUND-TRUTH GENERATION

(71) Applicant: KONINKLIJKE PHILIPS N.V., Eindhoven (NL)

(72) Inventors: Julien Thomas Senegas, Hamburg (DE); Sascha Krueger, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 369 days.

(21) Appl. No.: 17/624,662

(22) PCT Filed: Jul. 3, 2020

(86) PCT No.: PCT/EP2020/068791
§ 371 (c)(1),
(2) Date: Jan. 4, 2022

(87) PCT Pub. No.: WO2021/004924
PCT Pub. Date: Jan. 14, 2021

(65) Prior Publication Data
US 2022/0277835 A1    Sep. 1, 2022

(30) Foreign Application Priority Data
Jul. 5, 2019    (EP) ..................................... 19184615

(51) Int. Cl.
*G06K 9/00*    (2022.01)
*G06T 7/33*    (2017.01)
(Continued)

(52) U.S. Cl.
CPC ............... *G16H 30/40* (2018.01); *G06T 7/33* (2017.01); *G16H 50/20* (2018.01);
(Continued)

(58) Field of Classification Search
CPC ........ G16H 30/40; G16H 50/20; G16H 40/60; G16H 30/20; G06T 7/33;
(Continued)

(56) References Cited

U.S. PATENT DOCUMENTS 9,940,545 B2 *    4/2018    Rezaee ............. G06F 18/24323
10,499,992 B2 *    12/2019    Wei ......................... A61B 34/10
(Continued)

FOREIGN PATENT DOCUMENTS

AU    2017324627 B2 *    12/2019    ............... A61N 5/10
EP    3340093 A1    6/2018
(Continued)

OTHER PUBLICATIONS

PCT International Search Report, International application No. PCT/EP2020/068791, Oct. 7, 2020.
(Continued)

*Primary Examiner* — Shervin K Nakhjavan
(74) *Attorney, Agent, or Firm* — Larry Liberchuk

(57) ABSTRACT

In order to generate annotated ground truth data for training a machine learning model for inferring a desired scan configuration of an medical imaging system from an observed workflow scene during exam preparation, a system is provided that comprises a sensor data interface configured to access a measurement image of a patient positioned for an imaging examination. The measurement image is generated on the basis of sensor data obtained from a sensor arrangement, which has a field of view including at least part of an area, where the patient is positioned for imaging. The system further comprises a medical image data interface configured to access a medical image of the patient obtained from a medical imaging apparatus during the imaging examination. The patient is positioned in a given geometry with respect to a reference coordinate system of the medical imaging appa-
(Continued)

ratus. The system further comprises an exam metadata interface configured to access exam metadata of the imaging examination. The system further comprises a processing unit, configured to determine an association between one or more features in the measurement image and one or more features extracted from the medical image and/or from the exam metadata by mapping a point in a coordinate system of the medical image to a point in a coordinate system of the measurement image. The system further comprises an output interface, configured to be coupled to a training set database for adding the measurement image comprising data that labels the one or more associated features in the measurement image to the training set database for training the machine learning model.

12 Claims, 5 Drawing Sheets

(51) Int. Cl.
    *G16H 30/40*         (2018.01)
    *G16H 50/20*         (2018.01)

(52) U.S. Cl.
    CPC ............... *G06T 2207/10081* (2013.01); *G06T 2207/10088* (2013.01); *G06T 2207/10104* (2013.01); *G06T 2207/10116* (2013.01); *G06T 2207/20081* (2013.01); *G06T 2207/30004* (2013.01)

(58) Field of Classification Search
    CPC . G06T 2207/10081; G06T 2207/10088; G06T 2207/10104; G06T 2207/10116; G06T 2207/20081; G06T 2207/30004; A61B 6/5217; A61B 6/5247; A61B 6/563; A61B 6/545; G06F 18/214; G06N 3/04; G06N 3/08; G06N 20/00
    See application file for complete search history.

(56) References Cited

U.S. PATENT DOCUMENTS

| | | | |
|---|---|---|---|
| 10,783,634 B2 * | 9/2020 | Nye | G16H 30/40 |
| 11,331,039 B2 * | 5/2022 | Matsumoto | A61B 5/0073 |
| 11,478,212 B2 * | 10/2022 | Singh | A61B 5/7267 |
| 11,681,952 B2 * | 6/2023 | Fine | G06N 3/045 |
| | | | 382/103 |
| 11,748,899 B2 * | 9/2023 | Chang | A61B 5/0077 |
| | | | 600/408 |
| 2013/0342851 A1 | 12/2013 | Dresel | |
| 2015/0228071 A1 | 8/2015 | Jockel | |
| 2016/0128666 A1 | 5/2016 | Grasruck | |
| 2016/0306924 A1 | 10/2016 | Singh | |
| 2017/0035374 A1 * | 2/2017 | Schäfer | A61B 6/4441 |
| 2017/0100089 A1 | 4/2017 | Chang | |
| 2017/0143312 A1 | 5/2017 | Hedlund | |
| 2017/0311842 A1 | 11/2017 | Boettger | |
| 2017/0354385 A1 | 12/2017 | Lerch | |
| 2018/0046875 A1 * | 2/2018 | Caluser | A61B 6/584 |
| 2018/0228460 A1 | 8/2018 | Singh | |
| 2020/0058389 A1 | 2/2020 | Saalbach | |
| 2022/0254018 A1 * | 8/2022 | Zhang | A61B 5/0077 |

FOREIGN PATENT DOCUMENTS

| | | | | |
|---|---|---|---|---|
| JP | 2020520005 A | * | 7/2020 | ............ G06T 7/149 |
| WO | WO-2018087083 A1 | * | 5/2018 | ........... A61B 5/0064 |
| WO | WO2019067524 A1 | | 4/2019 | |

OTHER PUBLICATIONS

Pruessmann K.P. et al., "SENSE: Sensitivity Encoding for Fast MRI", Magnetic Resonance in Medicine 42:952-962 (1999).
Singh V. et al., "Estimating a Patient Surface Model for Optimizing the Medical Scanning Work-flow", MICCAI International Conference on Medical Image Computing and Computer Assisted Intervention) 2014 Part I, LNCS 8673, pp. 472-479, 2014.
Singh V. et al., "DARWIN: Deformable Patient Avatar Representation with Deep Image Net-work", MICCAI 2017 Part II, LNCS 10434, pp. 497-504, 2017.

* cited by examiner

SELF-LEARNING DISTRIBUTED SYSTEM WITH AUTOMATED GROUND-TRUTH GENERATION

FIELD OF THE INVENTION

The present invention relates to a system and a method for generating annotated ground truth data for training a machine learning model for inferring a desired scan configuration of an medical imaging system from an observed workflow scene during exam preparation. The invention further relates to a medical imaging system comprising the system, and to a computer readable medium comprising instructions for causing a processor system to perform the methods.

BACKGROUND OF THE INVENTION

In a number of cases, the appropriate preparation and execution of medical imaging examinations (e.g. in X-ray imaging) involves a technical operator manually selecting a parameter based on his appreciation of anatomical and physiological patient features. For example, the selection of the desired scan region is done in computer tomography (CT) imaging in two steps: first, defining the appropriate body region using a laser point, which determines the geometry of the scout scan, and then, selecting on the scout image the appropriate region of interest.

In order to reduce the total time of imaging examinations and to reduce the variability induced by manual operations, computer-based tools, such as machine learning, have been developed in recent years for determining a scan configuration for the medical imaging examinations. For example, US 2015/0228071 A1 describes that landmarks on the depth images can be identified using a trained machine learning algorithm.

However, in the above approaches, the algorithm needs to be developed and trained using data that have been labeled accordingly, mostly based on a manual or semi-automated process. This initial phase of ground truth generation is most often that factor that limits the final performance of the algorithm, either due to a limited number of accurately labeled input data or due to inaccuracies in the labelling. Another limitation is that the machine learning and deep learning systems are trained once on a subset of all possible data, and then applied in the field to new data without the possibility to further extend the training database. If data with new and not foreseen characteristics arise, either the system will perform poorly, or a new training based on new labelled data needs to be started.

SUMMARY OF THE INVENTION

There may be a need to provide a system for generating annotated ground truth data for training the machine learning model.

The object of the present invention is solved by the subject-matter of the independent claims, wherein further embodiments are incorporated in the dependent claims. It should be noted that the following described aspects of the invention apply also for the system, the method, the medical imaging system, and the computer readable medium.

A first aspect of the present invention provides a system for generating annotated ground truth data for training a machine learning model for inferring a desired scan configuration of an medical imaging system from an observed workflow scene during exam preparation, comprising:

an exam metadata interface, configured to access exam metadata of an imaging examination carried out with at least one medical imaging system, wherein the exam metadata comprises information about a configuration of the at least one medical imaging system;

a sensor data interface, configured to access a measurement image of a patient positioned in a given geometry with respect to a reference coordinate system of a medical imaging apparatus of the at least one medical imaging system for the imaging examination, wherein the measurement image is generated on the basis of sensor data obtained from a sensor arrangement, which has a field of view including at least part of an area, where the patient is positioned for imaging; and a medical image data interface, configured to access a medical image of the patient obtained from the medical imaging apparatus during the imaging examination; and a processing unit, configured to determine an association between one or more features in the measurement image and one or more features extracted from the medical image and/or from the exam metadata, by mapping a point in a coordinate system of the medical image to a point in a coordinate system of the measurement image; and an output interface, configured to be coupled to a training set database for adding the measurement image comprising data that labels the one or more associated features in the measurement image to the training set database for training the machine learning model.

In other words, the above system involves obtaining a measurement image of the patient in an imaging examination, which may be a routine examination or a research examination. The measurement image may be in the form of a depth image or an RGB image. The measurement image is acquired when the patient is positioned for the imaging examination, e.g., by lying or standing with the field of view of the imaging system. The measurement image does not necessarily have to include the whole body surface of the patient; it may relate to only part of the body surface of the patient, which is relevant for the imaging examination. For example, if an anatomy of interest is a neck of the patient, only the measurement image of the upper body of the patient may be captured by the sensor arrangement.

The above system also involves obtaining the exam metadata of the imaging examination. The exam metadata may be obtained from the log file of the medical imaging apparatus, such as an X-ray imaging apparatus, or a magnetic resonance (MR) imaging apparatus. The exam metadata may also be obtained from connected information, data archiving systems, such as a radiological information system (RIS), a hospital information system (HIS), and/or a picture archiving and communication system (PACS), and/or from other workstations. The exam metadata may comprise a configuration parameter of a scan volume that was planned by an operator, with which one or more features can be extracted from the medical image.

The above system further involves obtaining a medical image of the patient acquired by a medical imaging apparatus during the imaging examination. The medical image may comprise two-dimensional (2D), three-dimensional (3D), or four-dimensional (4D) images, acquired by various acquisition modalities including, but not limited to, X-ray imaging, MR imaging, CT imaging, positron-emission tomography (PET) imaging. Further examples of the medical imaging apparatus include a combined therapy/diagnostic apparatus, such as an MR-Linac apparatus, an MR proton therapy apparatus, and/or a cone beam CT apparatus.

A fully automated procedure may be used to compute one or more features, such as landmarks, organ boundaries, region-of-interest, and/or image labels in the medical image acquired by the medical image apparatus. One option is to use an image processing algorithm, such as an image detection algorithm that finds an approximate center and bounding box of the one or more features in the medical image. Another option is to derive the one or more features from a configuration parameter of a scan volume that was planned by an operator.

The extracted one or more features in the medical image, e.g., landmarks, organ boundaries, region-of-interest and/or image labels, may be mapped to the measurement image of the patient to determine one or more associated features in the measurement image. A relative geometry between the sensor arrangement and the at least one medical imaging system during the imaging examination may be used to map a point in the coordinate system of the image acquired by the sensor arrangement and a point in the coordinate system of the medical image acquired by the medical imaging apparatus. The term "relative geometry" may refer to a geometric relationship between the field of view of the sensor arrangement and the field of view of the imaging system. The measurement image with data that labels the one or more associated features in the measurement image may be added to the training data set database for the machine learning model.

By using the above system, the position and the size of an internal anatomy of interest can be automatically labelled in the measurement image to generate annotated ground truth data. The annotated ground truth data may be generated from routine examinations at one or more clinical sites. This continuous and unsupervised process of acquisitioning annotated ground truth data provides a basis for the generation of a large ground truth database, thereby overcoming the disadvantage of the limited number of training sets obtained by a manual or semi-automated process. The accuracy of the labelling may also be improved, as the associated features in the measurement image is transformed from the features in the medical images, which are extracted by an image detection algorithm or based on a configuration parameter of a scan volume that was planned by an operator, who is considered to be an expert. The large number of annotated ground truth data may be essential for training the machine learning model. For example, for deep learning approach it is essential to train the neural networks with a very large number of data to avoid overfitting effects, i.e. to ensure that the trained system well generalizes to unseen data. Another advantage of the system is that the annotated ground truth data is generated continuously from routine examinations and research examinations, thereby further and continuously extending the training set database. If data with new and not foreseen characteristics arise, or if the desired outcome of the trained system needs to be adapted, the continuously extending training set database may allow retaining of the machine learning model for changes happening overtime.

According to an embodiment of the present invention, the processing unit is configured to extract the one or more features from the medical image using an image processing algorithm and/or to derive the one or more features in the medical image from the exam metadata that comprises a configuration parameter of a scan volume that was planned by an operator.

In an example, the image processing algorithm may be an image segmentation algorithm that finds the outlines of the one or more features in the medical image. In another example, the image processing algorithm may be an image detection algorithm that finds an approximate centre and bounding box of the one or more features in the medical image. As a further example, the one or more features in the medical image may be derived from the exam metadata that comprises a configuration parameter, e.g. a geometry parameter, of a scan volume that was planned by an operator. Accordingly, no user interaction is required for identifying relevant features in the medical image.

According to an embodiment of the present invention, the system further comprises a control unit configured to perform at least one of the following functions: initiating the annotated ground truth data collection, interrupting the annotated ground truth data collection, and stopping the annotated ground truth data collection.

The system may be configured to perform continuous and unsupervised acquisition of annotated ground truth data for providing a basis for a desired generation of a large ground truth database and will allow retaining the machine learning model to accommodate for changes happening over time. A remote and/or local control unit may be provided that enables to interrupt or stop that data collection and the learning process at any time, for example, if the number of data collected is shown sufficient to fulfil the purpose of the data collection.

According to an embodiment of the present invention, the system further comprises a storage device for storing the training set database obtained from one or more clinical sites.

According to an embodiment of the present invention, the processing unit is configured to process the exam metadata to obtain an exam detail of the imaging examination comprising at least one of: an exam target anatomy, data relating to a patient setup and an exam preparation workflow comprising a patient orientation and laterality, a presence of a specific device used for the imaging examination, and/or a trajectory during an insertion of a patient support, data relating to an imaging workflow comprising a scan activity, and/or a motion of a patient support, and a method for temporal alignment of data from the distributed subcomponents. The output interface is configured to be coupled to the training set database for adding data that comprises the exam detail of the imaging examination to the training set database for training the machine learning model.

The exam detail of the imaging examination may comprise complementary information to the annotated measurement image. For example, the scanning position may be correlated to the patient orientation and laterality and/or the trajectory during insertion of the patient support. The scanning position may also be correlated to the scan activity, such as an intermittent table stop or a light visor activation. All scanning off-center and angulation trajectories may also be recorded and related to the scanning position. Therefore, by additionally adding the exam detail to the training set database, the machine learning model may be trained to better model the relation between the patient and the scanning position.

According to an embodiment of the present invention, the processing unit is configured to process the metadata to obtain non-image patient data of the patient. The non image patient data of the patient comprises at least one of: weight, BMI, height of the patient, an age of the patient, a gender of the patient, a medical condition of the patient comprising pregnancy, allergies to some contrast agents or others, and/or a presence of implants, a quantification of a fitness level of the patient, a breathing rate, a pulse rate a disease diagnostic associated with the patient, a medication record associated with the patient, and a vital parameter record associated with the patient. The output interface is configured to be coupled to the training set database for adding the non-image patient data of the imaging examination to the training set database for training the machine learning model.

The non-image patient data of the patient may comprise complementary information to the measurement image captured by the sensor arrangement. For example, the size of the lung is known to be correlated to the patient weight, age and gender and may be influenced by certain diseases like CORP. By additionally adding the non-patient image data obtained during the imaging procedure into the training set database, the machine learning model may be trained to better model the relation between the patient and the scan configuration, e.g. collimation settings, to be used in the exam preparation and/or in the imaging procedure.

According to an embodiment of the present invention, the sensor arrangement comprises at least one of: an optical sensor, a depth sensor, a thermal sensor, a pressure sensor, an ultrasound sensor, and an array of radio frequency sensors.

According to an embodiment of the present invention, the desired scan configuration comprises at least one of: a desired patient orientation and laterality, a desired scan position relative to the medical imaging apparatus, an acquisition parameter for the imaging examination, and a list of accessories relevant to the scan configuration.

In an example, the imaging system is a MR imaging system, and the acquisition parameter is at least one of a parameter specifying the positioning of the patient with respect to the MR imaging system, a geometry acquisition parameter, a selection parameter for a pre-set protocol, a SENSE factor, a SENSE direction, and LPH scan off-centers and orientation. The term "SENSE" refers to sensitivity encoding, which is described in the article "SENSE: Sensitivity Encoding for Fast MRP", by Klaas P. Pruessmann et al., Magnetic Resonance in Medicine 42:952-962 (1999). The SENSE factor is the undersampling factor. The SENSE direction is the direction of sensitivity encoding. In another example, the imaging system is an X-ray imaging. The acquisition parameter is at least one of a tube voltage, a tube current, a grid, a collimation window, and a geometry parameter of a collimator. In a further example, the imaging system is a CT imaging system. The acquisition parameter is at least one of a power supply level, a tube current, a dose modulation, a scan planning parameter, and a reconstruction parameter. Data relating to the motion of the patient support may be used to train the machine learning model to derive the optimal scan position which can minimize overall motion of the patient support. For example, the physical state and fitness of the patient in the non-image patient data may be relevant for training the machine learning model to determine the collimation settings, the exposure time settings, the tube voltage settings, the focal spot size settings, the selection of the X-ray sensitive areas for an X-ray imaging system. The annotate measurement image may be relevant for training the machine learning model to determine the parameter specifying the positioning of the patient with respect to the MR imaging system, the geometry acquisition parameter and LPH scan off-centers and orientation.

According to an embodiment of the present invention, the medical imaging apparatus comprises an X-ray imaging apparatus, an MR imaging apparatus, a CT imaging apparatus, a PET imaging apparatus.

According to an embodiment of the present invention, the medical imaging apparatus is a combined therapy/diagnostic apparatus comprising an MR-Linac apparatus, an MR proton therapy apparatus, and/or a cone beam CT apparatus.

A second aspect of the present invention provides a medical imaging system, comprising:
  a medical imaging apparatus, including a central system axis;
  a patient support, movable along the system axis;
  a sensor arrangement, configured to generate a measurement image of a patient positioned for an imaging examination, wherein the sensor arrangement has a field of view including at least part of an area, where the patient is positioned for imaging;
  a computing unit, configured to determine a desired scan configuration for performing an imaging examination of an exam target anatomy by applying a trained machine learning model to the measurement image, wherein the machine learning model has been trained with training data comprising annotated ground truth data generated from a system as described above and below for determining one or more scan parameters for the medical imaging apparatus.

By using machine learning for the measurement image, which has been trained using a training set database comprising the automatically generated ground truth data, the machine learning model will learn to predict the scan configuration by itself and thus eliminate the user interaction. For example, the machine learning model can be trained to connect the body surface in the measurement image with an internal anatomy of interest with the annotated measurement image in the training set database.

According to an embodiment of the present invention, the system further comprises a control unit, configured to apply the scan setting to control operation of the medical imaging apparatus and/or the patient support before or during image acquisition of the exam target anatomy.

According to an embodiment of the present invention, the machine learning model comprises at least one of: an artificial neural network, and a classification tree using at least one of Haar-like, scale-invariant feature transform (SIFT), and speed up robust feature (SURF) image features.

The classification tree may use other image features known to a person skilled in the art.

A further aspect of the present invention provides a method for generating annotated ground truth data for training a machine learning model for inferring a desired scan position from an observed workflow scene during exam preparation, comprising:
  accessing a measurement image of the patient positioned for an imaging examination carried out with at least one medical imaging system, wherein the patient is positioned in a given geometry with respect to a reference coordinate system of a medical imaging apparatus of the at least one medical imaging system, and wherein the measurement image is generated on the basis of sensor data obtained from a sensor arrangement, which has a field of view including at least part of an area, where the patient is positioned for imaging;
  accessing a medical image of the patient obtained from the medical imaging apparatus of the at least one medical imaging system during the imaging examination;
  accessing exam metadata of the imaging examination carried out with the at least one medical imaging system, wherein the exam metadata comprises information about a configuration of the at least one medical imaging system; and determining an association between one or more features in the measurement image and one or more features extracted from the medical image and/or from the exam metadata by mapping a point in a coordinate system of the medical image to a point in a coordinate system of the measurement image; and adding the measurement image comprising data that labels the one or more associated features in the measurement image to a training set database for the machine learning model.

A further aspect of the present invention provides a computer readable medium comprising transitory or non-transitory data representing instructions arranged to cause a processor system to perform the method.

These and other aspects of the present invention will become apparent from and be elucidated with reference to the embodiments described hereinafter.

BRIEF DESCRIPTION OF THE DRAWINGS

These and other aspects of the invention will be apparent from and elucidated further with reference to the embodiments described by way of examples in the following description and with reference to the accompanying drawings, in which FIG. 1 schematically shows a system for generating annotated ground truth data for training a machine learning model for inferring a desired scan configuration of an medical imaging system from an observed workflow scene during exam preparation.

Figure 1:
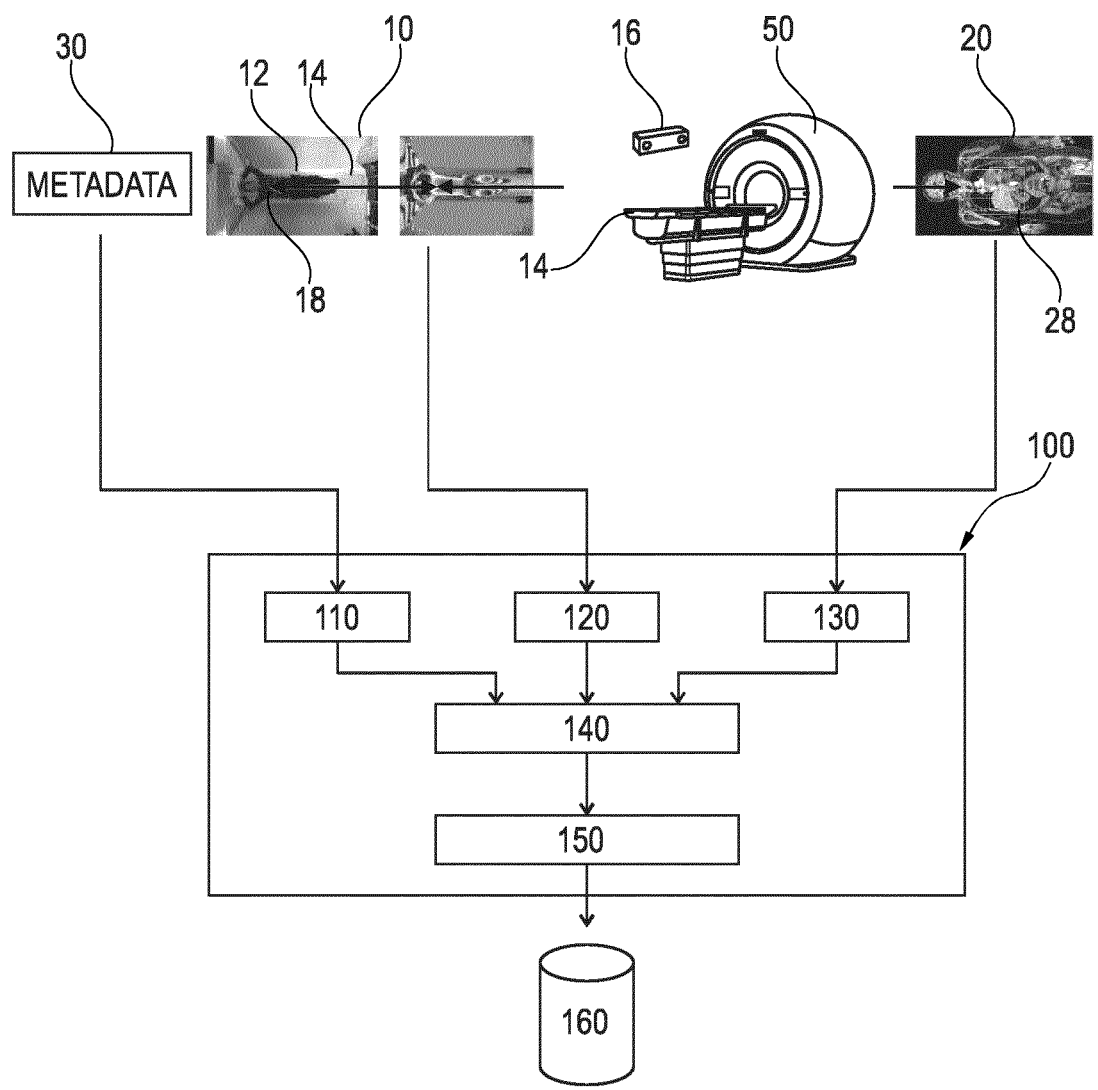

It should be noted that the figures are purely diagrammatic and not drawn to scale. In the figures, elements which correspond to elements already described may have the same reference numerals. Examples, embodiments or optional features, whether indicated as non-limiting or not, are not to be understood as limiting the invention as claimed.

DETAILED DESCRIPTION OF EMBODIMENTS

FIG. 1 schematically shows a system 100 which is configured for generating annotated ground truth data for training a machine learning model for inferring a desired scan configuration of an medical imaging system from an observed workflow scene during exam preparation. The desired scan configuration at least in part defines an imaging configuration of the medical imaging system prior to and/or during an imaging procedure with a patient. The system comprises an exam metadata interface 110, a sensor data interface 120, a medical image data interface 130, a processing unit 140, and an output interface 150.

Figure 3:
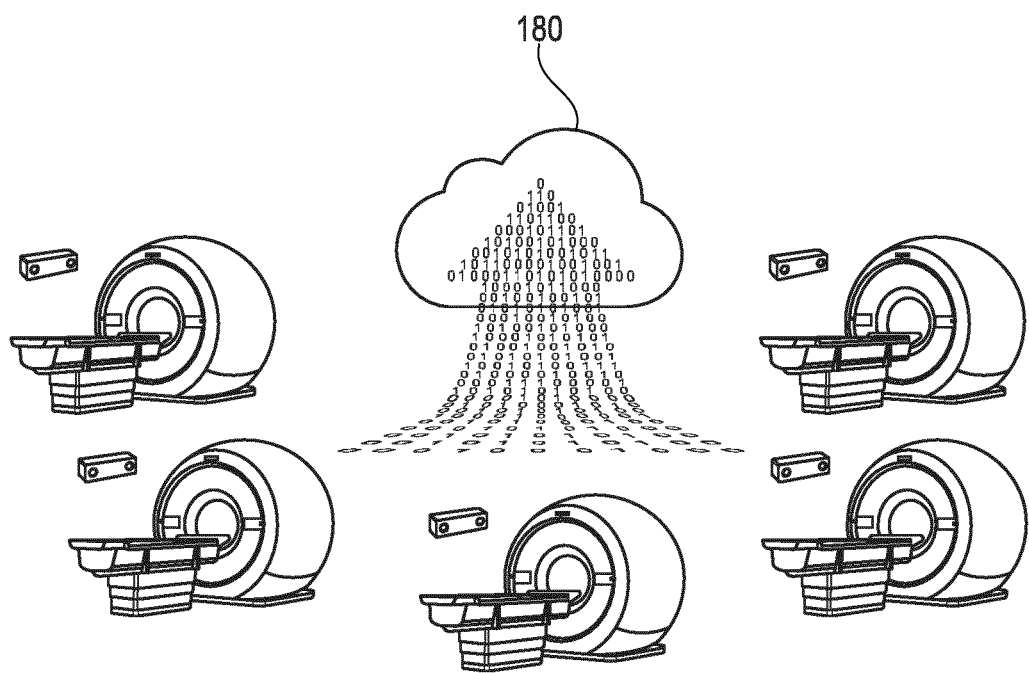
FIG. 3 schematically shows a storage device in form of a cloud storage for storing the training set database.

The exam metadata interface 110 is configured to access exam metadata 30 of an imaging examination carried out with at least one medical imaging system, such as multiple medical imaging system at at one or more clinical sites as shown in FIG. 3. The exam metadata comprises information about a configuration, e.g. scan and system configuration, of the at least one medical imaging system. In the example of FIG. 1, the exam metadata is obtained from a medical imaging apparatus 50 itself. In other examples, the exam metadata interface may access exam metadata from connected information, from data archiving systems such as radiological information system (RIS), a hospital information system (HIS), and/or a picture archiving and communication system (PACS), and/or from other workstations.

The sensor data interface 120 is configured to access a measurement image 10 of a patient 12 positioned in a given geometry with respect to a reference coordinate system of a medical imaging apparatus 50 of the at least one medical imaging system for the imaging examination, e.g., lying on a patient support 14 as show in the example of FIG. 1. The measurement image 10 is generated on the basis of sensor data obtained from a sensor arrangement 16. In the example of FIG. 1, the sensor arrangement comprises a depth camera. Further examples of sensors in the sensor arrangement 16 may include an optical sensor, a depth sensor, a thermal sensor, a pressure sensor embedded in the patient support 14, an ultrasound sensor e.g. embedded in the patient support 14, and/or an array of radio frequency sensors. The sensor arrangement 16 may be arranged remote from a medical imaging apparatus 50, e.g. on the ceiling of the room, such that the sensor arrangement has a field of view including at least part of an area, where the patient 12 is positioned for imaging. The sensor arrangement 16, such as a pressure sensor, may be embedded in the patient support 14 to achieve a field of view including at least part of an area, where the patient 12 is positioned for imaging. The sensor data interface 110 may take various forms, such as a network interface to a local area network, but also a video interface, e.g., HDMI, etc.

The medical image interface 130 is configured to access a medical image 20 of the patient 12 obtained from a medical imaging apparatus 50 during the imaging examination. The patient 12 is positioned in the given geometry with respect to the reference coordinate system of the medical imaging apparatus 50 for being imaged. In the example of FIG. 1, the medical imaging apparatus is an MR imaging apparatus. Further examples of the medical imaging apparatus 50 may include, but not limited to, an X-ray imaging apparatus, a CT imaging apparatus, and/or a PET imaging apparatus. The medical imaging apparatus may also be a combined therapy/diagnostic apparatus, such as an MR-Linac apparatus, an MR proton therapy apparatus, and a cone beam CT apparatus. The medical image 20 may also comprises localizer images or scout images, which are used in MR and CT studies to identify the relative anatomical position of a collection of cross-sectional images. The medical image interface 120 may take various forms, such as a network interface to a local area network, but also a video interface, e.g., HDMI, etc.

The processing unit 140 is configured to determine an association between one or more features 18 in the measurement image 10 and one or more features 28 extracted from the medical image 20 and/or from the exam metadata 30, by mapping a point in a coordinate system of the medical image 20 to a point in a coordinate system of the measurement image 10. The one or more features 28 extracted from the medical image 20 may include, but not limited to, landmarks, organ boundaries, region-of-interest and/or image labels in the medical images 20 acquired by the medical apparatus 50. In the example of FIG. 1, the features 28 extracted from the medical image 20 are indicated with bounding boxes. For example, the processing unit 140 may be configured to extract the one or more features 28 from the medical image 20 using an image processing algorithm, such as a detection algorithm that would find the approximate center and the bounding box of relevant features. Alternatively or additionally, the processing unit may be configured to extract the one or more features 28 from the exam metadata that comprises a configuration parameter of a scan volume that was planned by an operator. For example, the medical imaging apparatus 50 may comprise a manual graphical user interface (GUI) that allows an operator to select the scan position and the scan region for generating the scan parameter. The scan parameter may be used to extract the one or more features 28 from the medical image 20.

The output interface 150 is configured to be coupled to a training set database 160 for adding the measurement image 10 comprising data that labels the one or more features 18 in the measurement image 10 to the training set database 160 for training the machine learning model. The training set database 160 may be stored in an internal storage device of the system 100. Alternatively or additionally, the training set database 160 may be stored in an external storage device, e.g., in a cloud storage.

In this way, continuous and unsupervised acquisition of annotated ground truth data can be achieved for providing a basis for ideal generation of a large ground truth database. As no manual edition or labeling of input data to generate ground truth is required, time efficiency may be improved. Additionally, the ground truth database can be further and continuously extended. If data with new and not foreseen characteristics arise, or if the desired outcome of the trained system needs to be adapted, the machine learning model trained with the ground-truth database can accommodate for these changes happening over time. That is, due to the large amount of real data that can be collected via distributed systems, robustness with respect to variability in the input data can be improved. By using the data that labels the one or more features in the measurement image, the machine learning model may be trained to predict e.g. the size and position of an anatomy of interest, such as a lung of the patient. Once the position and size of the anatomy of interest is predicted, a desire scan configuration, e.g. proper collimation settings for the X-ray imaging system can be determined so to allow an optimal imaging of the anatomy of interest. The position and size of the anatomy of interest may also be used to infer a desired scan position of the patient with respective to the medical imaging apparatus of the at least one medical imaging system. With the desired scan position, a scan configuration with a parameter specifying the positioning of the patient with respect to the medical imaging apparatus of the at least one medical imaging system may be predict. This parameter may be used to automatically guide the patient support to move the patient to the desired scan position.

The system 100 may be embodied as, or in, a device or apparatus, such as a server, workstation, imaging system or mobile device. The device or apparatus may comprise one or more microprocessors or computer processors, which execute appropriate software. The processor of the system may be embodied by one or more of these processors. The software may have been downloaded and/or stored in a corresponding memory, e.g. a volatile memory such as RAM or a non-volatile memory such as flash. The software may comprise instructions configuring the one or more processors to perform the functions described with reference to the processor of the system. Alternatively, the functional units of the system, e.g., the sensor data interface, the medical image data interface, the exam metadata interface, the processing unit, may be implemented in the device or apparatus in the form of programmable logic, e.g., as a Field-Programmable Gate Array (FPGA). The sensor data interface, the medical image data interface, and the exam metadata interface may be implemented by respective interfaces of the device or apparatus. In general, each functional unit of the system may be implemented in the form of a circuit. It is noted that the system 100 may also be implemented in a distributed manner, e.g. involving different devices or apparatuses.

These annotated ground truth data may comprise further data that allows the machine learning model to determine further configuration parameters of the medical imaging system. For example, the processing unit 140 may be configured to process the exam metadata 30 to obtain an exam detail of the imaging examination. The exam detail may comprise exam target anatomy.

The image detail may comprise data relating to a patient setup and an exam preparation workflow, which may be used to train the machine learning model to recognize whether the patient is correctly prepared for the imaging examination. For example, data relating to the patient orientation and laterality may be used to train the machine learning model to recognize whether the patient is correctly positioned in a given geometry with respect to a reference coordinate system of the medical imaging apparatus. Data relating to a trajectory during an insertion of a patient support may be used to train the machine learning model to predict a path for inserting the patient support for the imaging examination.

The exam detail may further comprise data relating to an imaging workflow, which may be used to train the machine learning algorithm to select an acquisition parameter for the imaging examination. For example, An intermittent table stop or a light visor activation may be stored and related to the scanning position. All scanning off-center and angulation trajectories may be recorded and related to the scanning position. These data may be used to train the machine learning model to derive the optimal scanning position for an anatomy of interest.

The exam detail may further comprise a list of accessories relevant to the scan configuration. Examples of the specific devices may include, a MR coils, a physiology device, such as an ECG recording device, a pulse oximeter, a respiratory belt, an injector, an injection line, a headphone.

The exam detail may further comprise a method for temporal alignment of data from the distributed subcomponents, e.g. using timestamps or synchronized/triggered data sampling, which may be used to train the machine learning model to recognize whether the workflow during the exam preparation and/or during the imaging procedure is correctly followed.

The output interface 150 is configured to be coupled to the training set database 160 for adding data that comprises the exam detail of the imaging examination to the training set database for training the machine learning model.

In a further example, the metadata processing unit 140 is configured to process the metadata 30 to obtain non-image patient data of the patient. The non-image patient data of the patient comprises at least one of weight, BMI, height of the patient, an age of the patient, a gender of the patient, a medical condition of the patient comprising pregnancy, allergies to some contrast agents or others, and/or a presence of implants, a quantification of a fitness level of the patient, a breathing rate, a pulse rate a disease diagnostic associated with the patient, a medication record associated with the patient, and a vital parameter record associated with the patient. The output interface is configured to be coupled to the training set database for adding data that comprises the exam detail of the imaging examination to the training set database for training the machine learning model. For example, the age, gender, physical state, fitness, and medical condition of the patient may be relevant for training the machine learning model to determine the collimation settings, the exposure time settings, the tube voltage settings, the focal spot size settings, and the selection of the X-ray sensitive areas for an X-ray imaging system.

Figure 2:
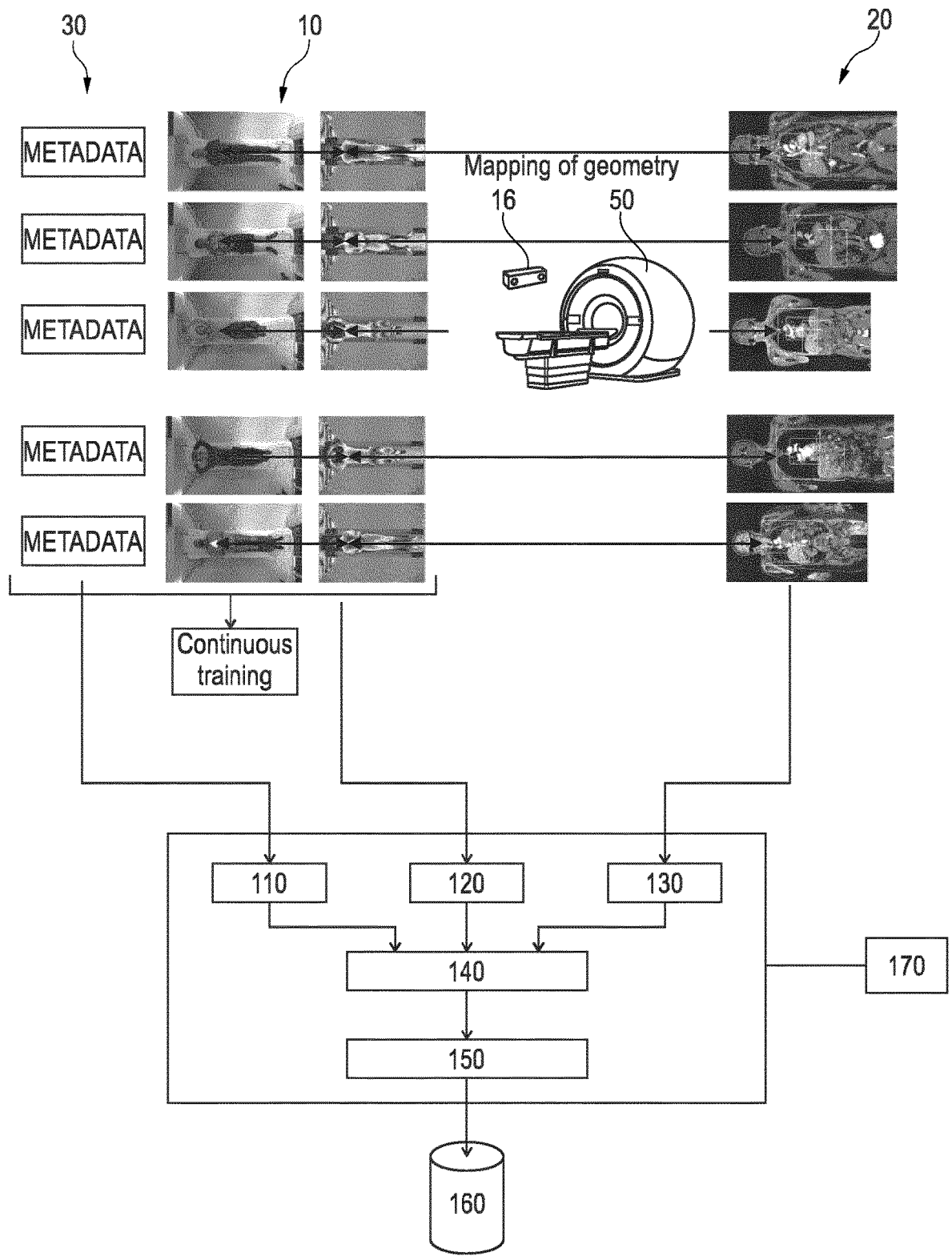
FIG. 2 shows a system that acquires the annotated ground truth data continuously from a routine examination.

The system 100 may be installed in a hospital or other environment allowing scanning under clinical-like conditions to collect data from a routine examination and a research examination at one or more clinical sites. FIG. 2 shows the system 100 that acquires the annotated ground truth data continuously from a routine examination. The system 100 may further comprise a control unit 170 configured to perform at least one of the following functions: initiating the annotated ground truth data collection, interrupting the annotated ground truth data collection, and stopping the annotated ground truth collection.

The system may comprise a storage device 180 for storing the training set database obtained from one or more clinical sites. FIG. 3 shows an example of the storage device in form of a cloud storage for storing the training set database 160. In other words, annotated ground truth data may be collected and processed continuously on request and upon agreement with one or more clinical sites. The annotated ground truth data may be shared and aggregated, e.g. via cloud technology as shown in FIG. 3. This may be done in a way which is compliant with regulation on privacy data, for example, by ensuring that the input data are anonymized and that only an intermediate layer of processed data is shared and stored, in which the anonymity is guaranteed. For example, only the depth differences at randomly selected image pixels of the depth sensor image are computed together with the pixel coordinates of the segmented boundary of a target organ in the corresponding medical image.

Figure 4:
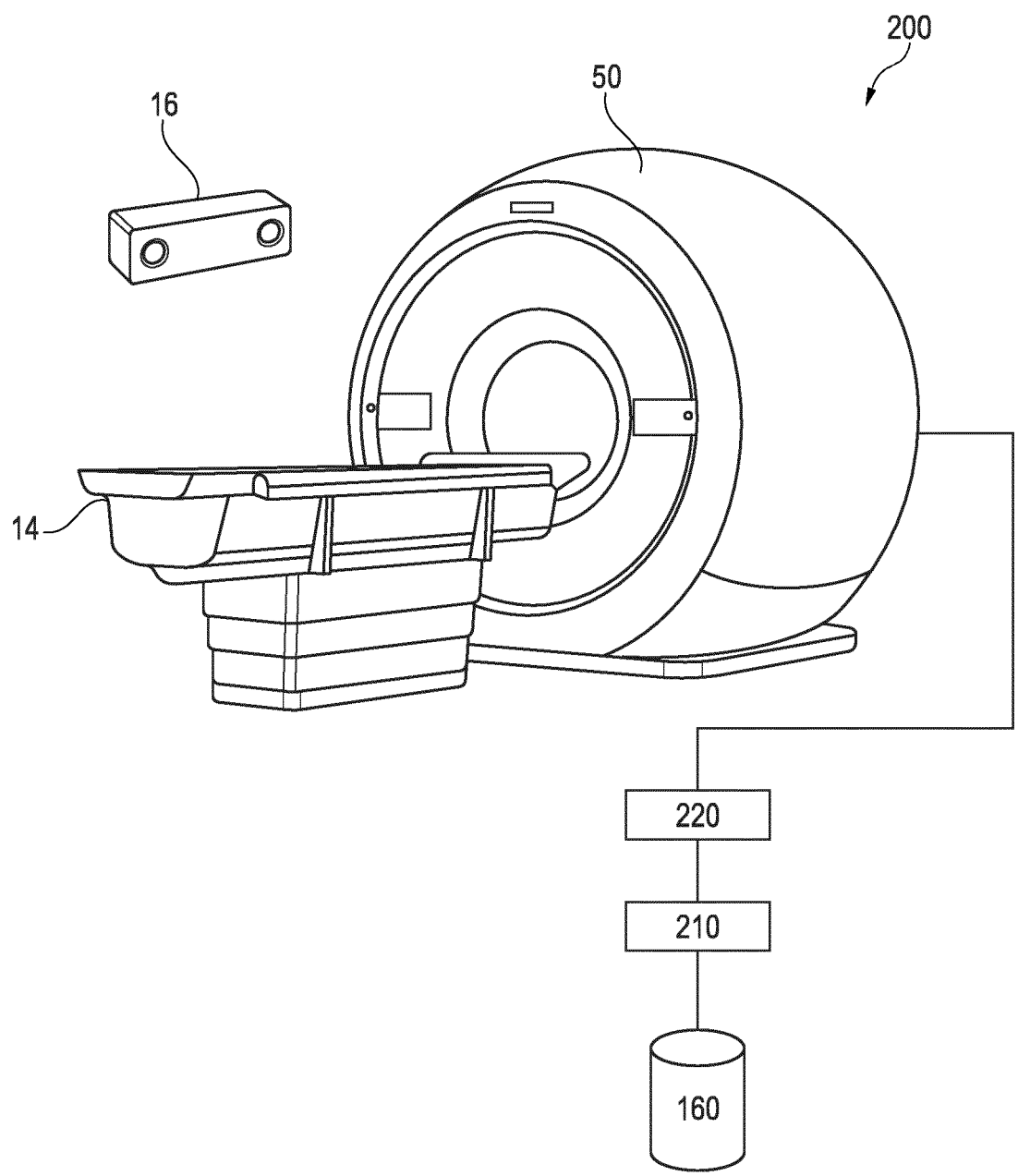
FIG. 4 schematically shows a medical imaging system.

FIG. 4 schematically shows a medical imaging system 200. The medical imaging system comprises a medical imaging apparatus 50, including a central system axis, a patient support 14, movable along the system axis, a sensor arrangement 16, and a computing unit 210.

The sensor arrangement 16, such as a camera or a thermal sensor, is configured to generate a measurement image of a patient positioned for an imaging examination. The sensor arrangement has a field of view including at least part of an area, where the patient is positioned for imaging.

The computing unit 210 is configured to determine a desired scan configuration for performing an imaging examination of an exam target anatomy by applying a trained machine learning model to the measurement image. The machine learning model has been trained with training data comprising annotated ground truth data generated from a system as described above for determining one or more scan parameters for the medical imaging apparatus 50. In an example, the machine learning model may be an artificial neural network. In another example, the machine learning model may be a classification tree using at least one of Haar-like, SIFT, SURF, image features and other image features known to a person skilled in the art.

The scan configuration may comprise a desired patient orientation and laterality, a desired scan position relative to the medical imaging apparatus, and/or an acquisition parameter for the imaging examination as described above.

Optionally, the medical imaging system further comprises a control unit 220 configured to apply the scan setting to control operation of the medical imaging apparatus and/or the patient support before or during image acquisition of the exam target anatomy. With the control unit, an automated work flow for exam preparation and imaging examination can be realized.

Figure 5:
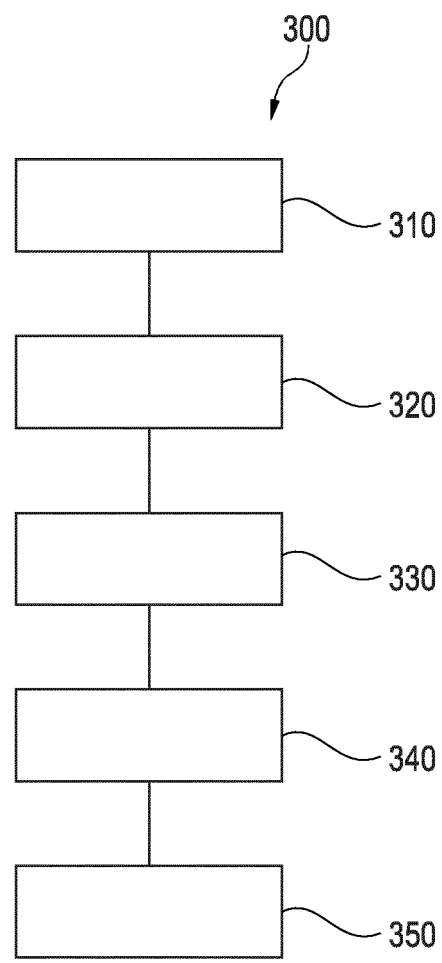
FIG. 5 shows a flow chart of a method for generating annotated ground truth data for training a machine learning model for inferring a desired scan configuration of an medical imaging system from an observed workflow scene during exam preparation.

FIG. 5 shows a method 300 for generating annotated ground truth data for training a machine learning model for inferring a desired scan position from an observed workflow scene during exam preparation. The method 300 may, but not need to, correspond to an operation of the system 100 as described with reference to FIG. 1 and others.

In step 310, a measurement image of the patient positioned for an imaging examination carried out with at least one medical imaging system, e.g. multiple medical imaging systems shown in FIG. 3, is obtained. The patient is positioned in a given geometry with respect to a reference coordinate system of a medical imaging apparatus of the at least one medical imaging system. The measurement image is generated on the basis of sensor data obtained from a sensor arrangement, which has a field of view including at least part of an area, where the patient is positioned for imaging. The measurement image may be captured by a sensor arrangement that comprises at least one of an optical sensor, a depth sensor, a thermal sensor, a pressure sensor, an ultrasound sensor, and an array of radio frequency sensors.

In step 320, a medical image of the patient may be obtained from a medical imaging apparatus of the at least one medical imaging system during the imaging examination. The patient is positioned in a given geometry with respect to a reference coordinate system of the medical imaging apparatus. The medical image may be acquired by a medical imaging apparatus selected from an X-ray imaging apparatus, an MR imaging apparatus, a CT imaging apparatus, and/or a PET imaging apparatus. Further examples of the medical imaging apparatus may include a combined therapy/diagnostic apparatus, such as an MR-Linac apparatus, an MR proton therapy apparatus, and/or a cone beam CT apparatus.

In step 330, exam metadata of the imaging examination carried out with the at least one medical imaging system may be obtained. The exam metadata comprises information about a configuration of the at least one medical imaging system. The exam metadata may be obtained from the medical imaging apparatus itself, from connected information, from data archiving systems such as RIS, HIS, and/or PACS, and/or from other workstations. Optionally, the metadata may comprise an exam detail of the imaging examination, such as an exam target anatomy, data relating to a patient setup and an exam preparation workflow comprising a patient orientation and laterality, a presence of a specific device used for the imaging examination, and/or a trajectory during an insertion of a patient support, data relating to an imaging workflow comprising a scan activity, and/or a motion of a patient support, and a method for temporal alignment of data from the distributed subcomponents. As a further option, the exam metadata may comprise non-image patient data of the patient, such as a weight of the patient, an age of the patient, a gender of the patient, a medical condition of the patient comprising pregnancy, allergies to some contrast agents or others, and/or a presence of implants, a quantification of a fitness level of the patient, a breathing rate, a pulse rate a disease diagnostic associated with the patient, a medication record associated with the patient, and a vital parameter record associated with the patient.

In step 340, an association between one or more features in the measurement image and one or more features extracted from the medical image and/or from the exam metadata is determined by mapping a point in a coordinate system of the medical image to a point in a coordinate system of the measurement image. Optionally, the one or more features may be extracted from the medical image using an image processing algorithm. As another option, the one or more features in the medical image may be derived from the exam metadata that comprises a configuration parameter of a scan volume that was planned by an operator.

In step 350, the measurement image comprising data that labels the one or more features in the measurement image is added to a training set database for the machine learning model.

It will be appreciated that the above operation may be performed in any suitable order, e.g., consecutively, simultaneously, or a combination thereof, subject to, where applicable, a particular order being necessitated, e.g., by input/output relations.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for generating annotated ground truth data for training a machine learning model for inferring a desired scan configuration of a medical imaging apparatus from an observed workflow scene during exam preparation, comprising:
   a memory; and
   one or more processors coupled with the memory and configured to:
   access exam metadata of an imaging examination carried out with the medical imaging apparatus, wherein the exam metadata comprises information about a configuration of the medical imaging apparatus;
   access a measurement image of a patient positioned in a given geometry with respect to a reference coordinate system of the medical imaging apparatus for the imaging examination, wherein the measurement image is generated on the basis of sensor data obtained from a sensor arrangement, which has a field of view including at least part of an area where the patient is positioned for imaging;
   access a medical image of the patient obtained from the medical imaging apparatus during the imaging examination;
   determine an association between one or more features in the measurement image and one or more features extracted from the medical image and/or from the exam metadata by mapping a point in a coordinate system of the medical image to a point in a coordinate system of the measurement image; and
   add the measurement image comprising data that labels the one or more associated features in the measurement image to a training set database for training the machine learning model.

2. The system according to claim 1, wherein the one or more processors are further configured to extract the one or more features from the medical image using an image processing algorithm or derive the one or more features in the medical image from the exam metadata that comprises a configuration parameter of a scan volume that was planned by an operator.

3. The system according to claim 1, wherein the one or more processors are further configured to perform at least one of:
   initiating the annotated ground truth data collection;
   interrupting the annotated ground truth data collection; and
   stopping the annotated ground truth data collection.

4. The system according to claim 1, further comprising:
   a storage for storing the training set database obtained from one or more clinical sites.

5. The system according to claim 1, wherein the one or more processors are further configured to process the exam metadata to obtain an exam detail of the imaging examination comprising at least one of:
   an exam target anatomy;
   data relating to a patient setup and an exam preparation workflow comprising a patient orientation and laterality, a presence of a specific device used for the imaging examination, and/or a trajectory during an insertion of a patient support;
   data relating to an imaging workflow comprising a scan activity, and/or a motion of a patient support; and
   a method for temporal alignment of data from the distributed subcomponents; and
   wherein the one or more processors are further configured to be coupled to the training set database for adding data that comprises the exam detail of the imaging examination to the training set database for training the machine learning model.

6. The system according to claim 1, wherein the one or more processors are further configured to process the metadata to obtain non-image patient data of the patient comprising at least one of:
   weight, BMI, height of the patient;
   an age of the patient;
   a gender of the patient;
   a medical condition of the patient comprising pregnancy, allergies to some contrast agents or others, and/or a presence of implants;
   a quantification of a fitness level of the patient;
   a breathing rate;
   a pulse rate;
   a disease diagnostic associated with the patient;
   a medication record associated with the patient; and
   a vital parameter record associated with the patient; and
   wherein the one or more processors are further configured to be coupled to the training set database for adding the non-image data to the training set database for training the machine learning model.

7. The system according to claim 1, wherein the sensor arrangement comprises at least one of: an optical sensor, a depth sensor, a thermal sensor, a pressure sensor, an ultrasound sensor, and an array of radio frequency sensors.

8. The system according to claim 1, wherein the desired scan configuration comprises at least one of:
   a desired patient orientation and laterality;
   a desired scan position relative to the medical imaging apparatus;
   an acquisition parameter for the imaging examination; and
   a list of accessories relevant to the scan configuration.

9. The system according to claim 1, wherein the medical imaging apparatus comprises:
   an X-ray imaging apparatus;
   a magnetic resonance (MR) imaging apparatus;
   a computed tomography (CT) imaging apparatus; and/or
   a positron-emission tomography (PET) imaging apparatus.

10. The system according to claim 1, wherein the medical imaging apparatus is a combined therapy/diagnostic apparatus comprising:
    an MR-Linac apparatus;
    an MR proton therapy apparatus; and/or
    a cone beam CT apparatus.

11. A method for generating annotated ground truth data for training a machine learning model for inferring a desired scan position from an observed workflow scene during exam preparation, the method comprising:
    accessing a measurement image of a patient positioned for an imaging examination carried out with a medical imaging apparatus, wherein the patient is positioned in a given geometry with respect to a reference coordinate system of the medical imaging apparatus, and wherein the measurement image is generated on the basis of sensor data obtained from a sensor arrangement which has a field of view including at least part of an area where the patient is positioned for imaging;
    accessing a medical image of the patient obtained from the medical imaging apparatus during the imaging examination;
    accessing exam metadata of the imaging examination carried out with the medical imaging apparatus, wherein the exam metadata comprises information about a configuration of the medical imaging apparatus;
    determining an association between one or more features in the measurement image and one or more features extracted from the medical image and/or from the exam metadata by mapping a point in a coordinate system of the medical image to a point in a coordinate system of the measurement image; and
    adding the measurement image comprising data that labels the one or more associated features in the measurement image to a training set database for the machine learning model.

12. A non-transitory computer-readable medium for storing executable instructions, which cause a method to be performed to generate annotated ground truth data for training a machine learning model for inferring a desired scan position from an observed workflow scene during exam preparation, the method comprising:
    accessing a measurement image of a patient positioned for an imaging examination carried out with a medical imaging apparatus, wherein the patient is positioned in a given geometry with respect to a reference coordinate system of the medical imaging apparatus, and wherein the measurement image is generated on the basis of sensor data obtained from a sensor arrangement which has a field of view including at least part of an area where the patient is positioned for imaging;
    accessing a medical image of the patient obtained from the medical imaging apparatus during the imaging examination;
    accessing exam metadata of the imaging examination carried out with the medical imaging apparatus, wherein the exam metadata comprises information about a configuration of the medical imaging apparatus;
    determining an association between one or more features in the measurement image and one or more features extracted from the medical image and/or from the exam metadata by mapping a point in a coordinate system of the medical image to a point in a coordinate system of the measurement image; and adding the measurement image comprising data that labels the one or more associated features in the measurement image to a training set database for the machine learning model.

* * * * *